United States Patent
Harris et al.

(10) Patent No.: US 9,393,269 B2
(45) Date of Patent: *Jul. 19, 2016

(54) RAPID INFUSION OF AUTOLOGOUS BONE MARROW DERIVED STEM CELLS

(71) Applicant: CESCA THERAPEUTICS, Rancho Cordova, CA (US)

(72) Inventors: Kenneth Harris, Los Angeles, CA (US); Dalip Sethi, San Leandro, CA (US); Venkatesh Ponemone, Hyderabad (IN); Gary R. Cohan, Los Angeles, CA (US)

(73) Assignee: Cesca Therapeutics, Inc., Rancho Cordova, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/297,557

(22) Filed: Jun. 5, 2014

(65) Prior Publication Data
US 2014/0286869 A1  Sep. 25, 2014

Related U.S. Application Data (60) Division of application No. 14/296,360, filed on Jun. 4, 2014, which is a continuation of application No. PCT/US2014/010745, filed on Jan. 8, 2014.

(60) Provisional application No. 61/751,846, filed on Jan. 12, 2013.

(51) Int. Cl.
| | |
|---|---|
| *A61K 35/28* | (2015.01) |
| *A61B 5/145* | (2006.01) |
| *A61K 45/06* | (2006.01) |
| *A61K 49/00* | (2006.01) |
| *A61K 35/44* | (2015.01) |
| *A61K 38/55* | (2006.01) |

(52) U.S. Cl.
CPC ............. *A61K 35/28* (2013.01); *A61B 5/14503* (2013.01); *A61K 35/44* (2013.01); *A61K 38/55* (2013.01); *A61K 45/06* (2013.01); *A61K 49/0004* (2013.01)

(58) Field of Classification Search
None
See application file for complete search history.

(56) References Cited

U.S. PATENT DOCUMENTS

| | | | |
|---|---|---|---|
| 7,794,705 B2 * | 9/2010 | Pecora et al. | 424/93.7 |
| 2002/0037278 A1 * | 3/2002 | Ueno et al. | 424/93.7 |
| 2006/0008450 A1 * | 1/2006 | Verfaillie et al. | 424/93.21 |
| 2006/0246042 A1 * | 11/2006 | Davies | 424/93.7 |
| 2009/0143296 A1 | 6/2009 | Anversa | |
| 2010/0112691 A1 | 5/2010 | Green et al. | |
| 2010/0143317 A1 | 6/2010 | Pecora et al. | |
| 2010/0266561 A1 | 10/2010 | Poznansky et al. | |
| 2011/0076255 A1 | 3/2011 | Pecora et al. | |
| 2012/0301538 A1 | 11/2012 | Gordon-Beresford et al. | |
| 2013/0029370 A1 * | 1/2013 | Coelho | 435/29 |

OTHER PUBLICATIONS

Strauer et al, Circulation, 2002, vol. 106, pp. 1913-1918.*
International Search Report and Written Opinion dated Mar. 19, 2014 for International Application No. PCT/US2014/010745.
Delewi, et al., Impact of intracoronary bone marrow cell therapy on left ventricular function in the setting of ST-segment elevation myocardial infarction: a collaborative meta-analysis, European Heart Journal, Sep. 11, 2013, doi:10.1093/eurheartj/eht372.
Tendera, et al., Intracoronary infusion of bone marrow-derived selected $CD34^+CXCR4^+$ cells and non-selected mononuclear cells in patients with acute STEMI and reduced left ventricular ejection fraction: results of randomized, multicentre Myocardial Regeneration by Intracoronary Infusion of Selected Population of Stem Cells in Acute Myocardial Infarction (REGENT) Trial, European Heart Journal, Feb. 10, 2009, 30:1313-21.
Steinberg, et al. Effect of High Concentrations of Leukocytes on Whole Blood Viscosity, Blood, Feb. 25, 1971, 38: 299-301.
Baskurt, et al. Blood Rheology and Hemodynamics, Seminars in Thrombosis and Hemostasis, 29(5):435-450, 2003.
Sharma, et al. Cellular Volume and Marker Expression in Human Peripheral Blood Apheresis Stem Cells, Cytometry Part A, Jan. 11, 2008, 73A:160-167.
Barnes, et al. Resistance to Fluid Shear Stress Is a Conserved Biophysical Property of Malignant Cells, PLOS ONE, Dec. 2012, 7(12):e50973.
Lichtman, et al. Rheology of Leukocytes, Leukocyte Suspensions, and Blood in Leukemia, Possible Relationship to Clinical Manifestations, The Journal of Clinical Investigation, Feb. 1973, 52:350-358.
Chao-Hung Ho, White Blood Cell and Platelet Counts Could Affect Whole Blood Viscosity, Journal of the Chinese Medical Association, Aug. 2004, 67:394-397.
Gurkan, Umut Atakan, et al., The Mechanical Environment of Bone Marrow: A Review, Annals of Biomedical Engineering, vol. 36, No. 12, Dec. 2008.

* cited by examiner

*Primary Examiner* — Allison Fox
(74) *Attorney, Agent, or Firm* — Knobbe Martens Olson & Bear LLP (57) ABSTRACT

The present invention relates to a method and composition for the aspiration, processing, testing and infusion of bone marrow derived stem cells, as an adjuvant treatment in cardiovascular disorders. More specifically, the invention provides for the methods and compositions for the aspiration, analysis, processing, infusate preparation and infusion of bone-marrow derived stem cells, particularly in a rapid point-of-care environment, wherein a centrifugal fractionation and optically monitored separation of the bone marrow yield desired cellular product in the desired concentration and viscosity.

49 Claims, 4 Drawing Sheets

RAPID INFUSION OF AUTOLOGOUS BONE MARROW DERIVED STEM CELLS

RELATED APPLICATIONS

The present application is a divisional application of U.S. application Ser. No. 14/296,360, filed Jun. 4, 2014; which is a continuation application of PCT Application No. PCT/US2014/010745, filed Jan. 8, 2014; which claims priority to U.S. Provisional Application Ser. No. 61/751,846, filed Jan. 12, 2013, all of which are hereby expressly incorporated by reference in their entireties.

FIELD OF THE INVENTION

The present invention relates to a rapid point-of-care approach for aspirating, isolating, testing, and delivering a cell population and accompanying factors obtained from bone marrow in a pre-determined dose and viscosity to a subject and compositions that have a cell population, which includes bone marrow stem cells and/or progenitor cells, an anticoagulant, and a viscosity of less than or equal to 5.0 centipoise (cP) measured at 37° C.

BACKGROUND OF THE INVENTION

Cardiovascular disease (CVD) is the number one cause of morbidity and mortality worldwide. An estimated 17.3 million people died from CVDs in 2008, representing 30% of all global deaths. Of these deaths, an estimated 7.3 million were due to coronary heart disease and 6.2 million were due to stroke. More remarkably, low- and middle-income countries are disproportionally affected, driving the need for regenerative therapies in lieu of chronic drug treatment regimens and such regenerative therapies must be offered in formats eliminating the need for high cost laboratory infrastructure or extensive multi-hour usage of vascular catheter labs. Over 80% of CVD deaths take place in low- and middle-income countries and occur almost equally in men and women. In the progression of CVDs, plaque lesions develop in arteries that result in the narrowing of vessels, and in severe cases they break open and create a blockage of blood flow (ischemia) to a vital part of the heart, brain or limb. Such ischemia may be reversed if treated within a short period of time by reperfusion therapy and further by the infusion of adult tissue derived stem cells with or without the presence of extracellular factors. Despite significant advances in medical therapy and revascularization strategies, the prognosis of certain patients with Acute Myocardial Infarction (AMI), Chronic Heart Failure (CHF), Critical Limb Ischemia (CLI) and Ischemic Brain Injury (Stroke) remains dismal without the introduction of early biological repair intervention.

Along with reperfusion, adjuvant stem cell therapy has been shown to be potentially efficacious in the repair and regeneration of damaged tissue of heart, brain and limbs from ischemic injury. These stem/progenitor cells can be isolated from different sources and one such source is bone-marrow. The autologous, bone-marrow derived in one case, peripheral blood derived in the second case, and adipose derived in the third, adult stem/progenitor cells circumvent the ethical and legal issues related to embryonic stem cells. Further, it also terminates the risk of transmitting diseases and immune rejection. The regenerative potential of autologous stem cells, specifically adipose or peripheral blood, and most specifically bone marrow derived cellular product is highly influenced by the aspiration, processing, and delivery technique employed. Anticoagulant plays a crucial role in the overall efficacy of regenerative cell therapy, and extended exposure to anticoagulant has been shown to have a negative impact on the "stemness" of the cells. The use of an anticoagulant in the aspiration syringe and processing devices keeps the bone-marrow in a non-coagulated state, which allows proper stratification, isolation and infusion of stem/progenitor cells to treat clinical conditions. Anticoagulant also inhibits to varying degrees the formation of microthrombae, which if injected into the patient can cause adverse events. It is also understood that the addition of any chemical entity in the presence of proteins or cells ("Biologicals") may have an effect on the structure or function of the Biologicals. Therefore, the anticoagulant used, the concentration used, and the time of cell exposure to the anticoagulant individually and potentially, cumulatively, plays a crucial role in the overall outcome of the efficacy and safety of stem cell therapy. The ideal stem cell compatible anticoagulant must be in the optimal concentration ratio balance to keep the cell therapy concentrate or infusate in the anti-coagulated state for a defined period of time to complete the interventional procedure and also reduce or eliminate the intravascular formation of thrombae while minimizing the risk of peri-procedural bleeding and modulation of stem cells.

Heparins are the most commonly used anticoagulant agents for bone-marrow aspiration. It has, however, been reported that heparin can interfere with the mobilization and homing mechanism(s) of stem and/or progenitor cells thereby impairing the functional therapeutic capacity of these cells. Moreover, heparins are associated with high rates of peri-procedural bleeding, which may be related to their inability to bind to clot-bound thrombin. Still further, heparins can get inactivated in-vivo by binding to platelet factor-4 (PF-4). Certain individuals expressing antibody to heparin-PF-4 complex can experience Heparin-Induced-Thrombocytopenia (HIT) on exposure to heparins.

The anti-coagulated bone marrow aspirate is in a heterogenous mixture containing Hematopoietic Stem Cells ("HSCs"), Mesenchymal Stem Cells (MSCs), Endothelial Progenitor Cells ("EPCs), CXCR4 positive cells, White Blood Cells ("WBCs"), Red Blood Cells ("RBCs'), platelets ("PLTs"), plasma with serum proteins and metabolites ("PLASMA"), and fat ("FAT") and is unsuitable for delivery in the raw aspirate form into a patient's vascular system. Furthermore, to properly define the therapeutic cell mixture constituency for reproducible therapeutic efficacy patient-to-patient, and to prepare a safe but dose specific volume of the therapeutic cell concentrate, the therapeutically effective cells (HSC's, MSC's, WBC's, EPC's and CXCR4 positive cells) must be purified, isolated or captured from the ineffective and undesired cells and fat in a short period of time to render a concentrated therapeutic dose of cells and factors at the point-of-care.

The purification of cells, and specifically WBCs containing the desired HSC's, EPC's, MSC's and other stem/progenitors cells, has historically been accomplished by placing the cells in a containment device and applying standard centrifugal stratification under a gravity force using either chemical density based methods or in automated chemical free systems. The cells of the bone marrow coming from the red marrow and stroma will stratify to their respective density under specific gravity force ("g force") in a defined period of time, and thus create layers of cells in the containment device from bottom to top wherein the RBCs (most dense) are on the bottom, followed by the nucleated RBC's and VSELs, the WBC's, PLTs, PLASMA, and FAT. Both of the methods simply harvest the buffy coat as typically defined as the cellular layer above the RBC/nucleated RBC fraction and below the PLT fraction.

The ideal cell purification process involves a closed minimally manipulated procedure for rapidly stratifying and isolating the desired HSCs, EPCs, MSCs plus other stem/progenitor cells, which may also be referred to as stem cells or MNCs or progenitor cells or bone marrow concentrate enriched in progenitor cells ($BMC_EPC$) throughout this document, away from the undesired mature RBCs and topping up the desired cell fraction with PLASMA to the proper volume and viscosity for safe and effective delivery into the vascular system via a stem cell friendly device such as an over the wire balloon catheter, or an intra-organ delivery cannula.

The delivery of stem cells via a catheter procedure is an ideal way of infusing cells proximally to the afflicted organ. However, trans-catheter passage of cells can potentially have a negative impact on the desired cells in several ways. First, the cells undergo varying shear stresses depending on their proximity to the lumen wall, the velocity of the injection, the radius of the lumen, and the viscosity of the fluid, and second since the lumen is a polymeric substrate its potential to impact cells and cell membranes, which come in contact through activation, binding or shedding can be important.

The transcatheter delivery of stem cells into the vascular system is desirably achieved by introduction of an intravascular catheter in the peripheral vasculature, and inducing transient ischemia in the targeted organ proximally or distally to the catheter tip by inflating an intravascular balloon to slow or stop blood flow for a pre-determined time. Such ischemia improves the cellular homing of the stem and progenitor cells to the ischemic tissue, and increases the opportunity for the cells initiating one or more processes including but not limited to tissue integration, cellular fusion, cellular differentiation, and/or paracrine factor release. Ischemia is best induced by inflating a compliant or non-compliant balloon to reduce or stop blood flow while taking extra care to minimize any endothelium wall damage from the balloon pressurization.

Thus, there is a need for an improved method and composition for the aspiration, processing, and delivery of bone marrow cells, such that the bone-marrow derived stem cells provide a safe and efficient adjuvant therapy for re-vascularization and or organ repair in ischemic disorders.

SUMMARY OF THE INVENTION

Fast and efficient methods and complete point-of-care kits for aspiration, processing, and infusion of autologous stem cells and factors isolated from bone marrow in a period of less than 90 minutes have been developed. In some embodiments, methods for bone-marrow harvesting and processing, comprise an amount or concentration of an anticoagulant, preferably bivalirudin, which minimizes clot formation for up to 90 minutes without affecting the efficacy of stem cell therapy.

Some embodiments described herein yield a desired mixture comprising stem and/or progenitor cells, which comprises buffy coat stem and/or progenitor cells, such as hematopoietic stem cells (HSCs), mesenchymal stem cells (MSCs), endothelial progenitor cells (EPCs), and CXCR4 positive cells with a reduced or lowered amount of RBC as compared to conventional cell populations obtained from bone marrow.

Some embodiments described herein provide for a rapid cellular infusate analysis within the point-of-care environment, ensuring an adequate and viable dose for the cellular therapy.

Some embodiments described herein infuse, at a controlled viscosity and flow rate through either manual or metered mechanism(s), a cell population having bone marrow-derived stem and/or progenitor cells at a viscosity, that is measured at normal human body temperature (e.g., a viscosity of 5.0 cP, 4.5 cP, 4.0 cP, 3.5 cP, 3.0 cP, 2.5 cP, 2.0 cP, 1.5 cP, or 1.0 cP at 37° C.), so as to ensure that a viable and potent cell dose can be delivered via a transcatheter injection while minimizing shear stress.

Some embodiments described herein infuse the aforementioned cell population mixture through a transcatheter comprising control mechanism for both proper and safe intravascular balloon inflation.

Some embodiments comprise an anticoagulant as the only added chemical beyond a sodium chloride buffer. In some embodiments the anticoagulant is bivalirudin. Unlike many anticoagulants, bivalirudin generates little or no hemolysis.

Embodiments of the invention also include a disposable centrifugal cell stratification device, which may have controlled valving, capable of responding to motor driven on and off positioning or may have a density functioning separation device such that bone marrow derived cell populations above or below the device may be harvested. Some embodiments comprise an optional on-board firmware for controlling the interrogation and harvest of certain cell populations within a multi-stratified zone driven by differences in a light source transmission value responding to pre-determined light units or an equivalency density separation device whose density equals the targeted cells density to mass ratio, a rapid analytical instrument verifying certain cell populations or cell dose and viscosity of certain populations, and an intravascularly placed balloon catheter where said balloon is inflated proximally to the target organ for a specified period stopping 80-100% blood flow to induce ischemia. In some embodiments the controlled minimal cell shearing infusion of harvested cells and factors through the cannula lumen at a rate of 0.5 mL to 2.5 mL per minute as controlled or metered by a device such as a mechanical pump or hand controlled method as interpreted by an in-line manual pressure meter results in a reduced degree of apoptosis or other cell death.

The disclosure is further summarized through reference to the embodiments listed below:

1. A composition comprising:
    (a) a first cell population that comprises bone marrow stem cells and/or progenitor cells,
    (b) an anticoagulant, and
    (c) an aqueous buffer and/or an autologous serum and/or an autologous plasma fraction,
    wherein the composition has a viscosity of not more than 5.0 centipoise (cP) measured at 37° C.
2. The composition of embodiment 1, wherein the first cell population that comprises bone marrow stem cells and/or progenitor cells is autologous.
3. The composition of embodiment 2, wherein the first cell population that comprises bone marrow stem cells and/or progenitor cells is from a medullary space within a bone of said patient.
4. The composition of embodiment 3, wherein the bone is an iliac crest, a femora, a tibiae, a spine, a sternum or a rib.
5. The composition of embodiment 3, wherein said first cell population that comprises bone marrow stem cells are from the medullary space within the iliac space.
6. The composition of any of embodiments 1-5, wherein said anticoagulant is selected from the group consisting of a coumarin, a vitamin K antagonist, an indirect thrombin inhibitor, heparin, a factor Xa inhibitor, a direct thrombin inhibitor, batroxobin, hemetin, a purified plant extract, EDTA, citrate, oxalate, and a nitrophorin.

7. The composition of any of embodiments 1-6, wherein said anticoagulant is a direct thrombin inhibitor.

8. The composition of any of embodiments 1-5, wherein said anticoagulant comprises bivalirudin.

9. The composition of embodiment 8, wherein said bivalirudin is provided from a stock solution having a concentration of 1 mg/mL to 50 mg/mL.

10. The composition of embodiment 8, wherein said bivalirudin is provided from a stock solution having a concentration of 5 mg/mL to 35 mg/mL.

11. The composition of embodiment 8, wherein said bivalirudin is provided from a stock solution having a concentration of 10 mg/mL to 25 mg/mL.

12. The composition of embodiment 8, wherein said bivalirudin is provided from a stock solution having a concentration of 18 mg/mL to 22 mg/mL.

13. The composition of embodiment 8, wherein said bivalirudin is provided from a stock solution having a concentration of 20 mg/mL.

14. The composition of embodiment 8, wherein said bivalirudin is present in said composition at a concentration of 1 mg/mL-3 mg/mL.

15. The composition of embodiment 8, wherein said bivalirudin is present in said composition at a concentration of 1.5 mg/mL-2.5 mg/mL.

16. The composition of embodiment 8, wherein said bivalirudin is present in said composition at a concentration of 1.8 mg/mL-2.2 mg/mL.

17. The composition of embodiment 8, wherein said bivalirudin is present in said composition at a concentration of 2.0 mg/mL.

18. The composition of any of embodiments 1-17, wherein said viscosity measured at 37° C. is 1.0 cP-5.0 cP.

19. The composition of any of embodiments 1-17, wherein said viscosity measured at 37° C. is 1.8 cP-3.0 cP.

20. The composition of any of embodiments 1-17, wherein said viscosity measured at 37° C. is 2.0 cP-2.5 cP.

21. The composition of any of embodiments 1-17, wherein said viscosity measured at 37° C. is 3.1 cP-5.0 cP.

22. The composition of any of embodiments 1-21, wherein said aqueous buffer comprises an ionic salt.

23. The composition of any of embodiments 1-21, wherein said aqueous buffer comprises sodium chloride.

24. The composition of any of embodiments 1-21, wherein said aqueous buffer comprises sodium chloride and the amount of said sodium chloride in said composition is 0.9%.

25. The composition of any of embodiments 1-24, wherein said cell population that comprises bone marrow cells comprises mononuclear cells that comprise at least a stem cell and/or progenitor cell selected from the group consisting of hematopoietic stem cells, mesenchymal stem cells, endothelial progenitor cells, and CXCR4 positive cells.

26. The composition of any of embodiments 1-25, wherein said cell population that comprises bone marrow cells comprises at least $10^7$ mononuclear cells.

27. The composition of any of embodiments 1-25, wherein said cell population that comprises bone marrow cells comprises not more than $10^9$ mononuclear cells.

28. The composition of any of embodiments 1-25, wherein said cell population that comprises bone marrow cells comprises at least $10^4$ hematopoietic stem cells.

29. The composition of any of embodiments 1-25, wherein said cell population that comprises bone marrow cells comprises at least $5 \times 10^2$ mesenchymal stem cells.

30. The composition of any of embodiments 1-25, wherein said cell population that comprises bone marrow cells comprises at least $5 \times 10^2$ endothelial progenitor cells.

31. The composition of any of embodiments 1-25, wherein said cell population that comprises bone marrow cells comprises at least $5 \times 10^3$ CXCR4 positive cells.

32. The composition of any of embodiments 1-31, wherein said cell population that comprises bone marrow cells comprises at least $10^7$ to not more than $10^9$ mononuclear cells, at least $10^4$ hematopoietic stem cells, at least $5 \times 10^2$ mesenchymal stem cells, at least $5 \times 10^2$ endothelial progenitor cells, and at least $5 \times 10^3$ CXCR4 positive cells.

33. The composition of any of embodiments 1-32, wherein said composition demonstrates an apoptosis or other cell death rate of not more than about 40% one hour after delivery at a flow rate of 2.5 mL/min, through a catheter having a lumen size of approximately 0.36 mm and using a 5 mL syringe holding pressure to 28.39 psi with a plunger force of 4.85 lbf.

34. The composition of any of embodiments 1-32, wherein said composition demonstrates an apoptosis or other cell death rate of not more than about 40% one hour after delivery through a catheter if subjected to a maximum shear of not more than 9101/second.

35. A method of making a regenerative cell composition comprising:
 (a) providing a first cell population that comprises bone marrow stem cells and/or progenitor cells;
 (b) mixing an anticoagulant with said first cell population so as to produce a composition comprising said first cell population and anticoagulant;
 (c) enriching bone marrow stem cells within said composition comprising said cell population and anticoagulant so as to produce a second cell population that comprises enriched bone marrow stem cells and/or progenitor cells;
 (d) isolating a fraction comprising said second cell population that comprises enriched bone marrow stem cells and/or progenitor cells; and
 (e) adjusting the viscosity of said fraction using a liquid to a viscosity of not more than 5.0 cP measured at 37° C. so as to make said regenerative cell composition.

36. The method of embodiment 35, wherein said first cell population that comprises bone marrow stem cells and/or progenitor cells comprises aspirated cells from bone marrow.

37. The method of embodiment 36, wherein said aspirated cells from bone marrow are aspirated through an aspiration needle having a needle/trocar of 8 to 14 gauge.

38. The method of embodiment 36, wherein said aspirated cells from bone marrow are aspirated through an aspiration needle having a needle/trocar of 10 to 12 gauge.

39. The method of embodiment 36, wherein said aspirated cells from bone marrow are aspirated through an aspiration needle having a needle/trocar of 11 gauge.

40. The method of any of embodiments 35-39, wherein said aspirated cells are aspirated through a needle/trocar at negative pressure of less than 20 psi.

41. The method of any of embodiments 35-39, wherein said aspirated cells are aspirated through a needle/trocar at negative pressure of less than 15 psi.

42. The method of any of embodiments 35-39, wherein said aspirated cells are aspirated through a needle/trocar at negative pressure of less than 10 psi.

43. The method of any of embodiments 35-39, wherein said aspirated cells are aspirated through a needle/trocar at negative pressure of less than 5 psi.

44. The method of embodiment 35, wherein said liquid is an autologous plasma fraction.

45. The method of embodiment 35, wherein said liquid is an autologous serum or plasma fraction comprising liquid from which said fraction comprising said second cell population that comprises enriched bone marrow stem cells and/or progenitor cells was isolated.

46. The method of embodiment 35, wherein said anticoagulant is contacted with said first cell population that comprises bone marrow stem cells and/or progenitor cells prior to obtaining said first cell population that comprises bone marrow stem cells and/or progenitor cells from a subject.

47. The method of embodiment 35, wherein said anticoagulant is contacted with said first cell population that comprises bone marrow stem cells subsequent to obtaining said first cell population that comprises bone marrow stem cells from said subject.

48. The method of embodiment 47, wherein the anticoagulant is mixed with said first cell population at least in part by manually agitating a container containing the first cell population and the anticoagulant.

49. The method of embodiment 48, wherein the agitating comprises rolling the container.

50. The method of any of embodiments 35-49, wherein the anticoagulant comprises bivalirudin.

51. The method of embodiment 50, wherein said bivalirudin is provided at a concentration of 1 mg/mL-3 mg/mL.

52. The method of embodiment 50, wherein said bivalirudin is provided at a concentration of 1.8 mg/mL-2.2 mg/mL.

53. The method of embodiment 50, wherein said bivalirudin is provided at a concentration of 2.0 mg/mL.

54. The method of any of embodiments 35-49, wherein said viscosity measured at 37° C. is 1.0 cP-5.0 cP.

55. The method of any of embodiments 35-49, wherein said viscosity measured at 37° C. is 1.8 cP-3.0 cP.

56. The method of any of embodiments 35-49, wherein said viscosity measured at 37° C. is 3.1 cP-5.0 cP.

57. The method of any of embodiments 35-49, wherein said liquid is an aqueous buffer that comprises an ionic salt.

58. The method of embodiment 57, wherein said aqueous buffer comprises sodium chloride.

59. The method of embodiment 58, wherein the amount of said sodium chloride in said regenerative cell composition is 0.9%.

60. A method of ameliorating ischemia or a condition associated with ischemia in a subject comprising:
    identifying a subject having an ischemia or a condition associated with ischemia;
    providing to said subject a composition comprising:
        (a) a first cell population that comprises bone marrow stem cells and/or stem cell progenitor cells,
        (b) an anticoagulant, and
        (c) an aqueous buffer and/or an autologous serum and/or an autologous plasma fraction,
    wherein the composition has a viscosity of not more than 5.0 centipoise (cP) measured at 37° C.; and
    determining an improvement in ischemia or said condition associated with ischemia, such as by measuring or observing in said subject an increased blood flow, an improvement in left ventricle ejection fraction, an improvement in cardiac output, a reduction in cardiac scar formation, an improvement in cardiac remodeling, an increase in angiogenesis, an increase in vascularity, an improvement in neural scar formation, or an increase in amputation-free survival rate.

61. The method of embodiment 60, wherein the composition is provided to said subject not more than 2 hours after said first cell population that comprises stem cells and/or progenitor cells is obtained.

62. The method of embodiment 60, wherein the composition is provided to said subject not more than 90 minutes after said first cell population that comprises bone marrow stem cells and/or progenitor cells is obtained.

63. The method of embodiment 60, wherein the composition is provided to said subject not more than 60 minutes after said first cell population that comprises bone marrow stem cells and/or progenitor cells is obtained.

64. The method of any of embodiments 60-63, wherein the blood flow at an ischemic tissue of said subject is blocked for 1-3 minutes.

65. The method of any of embodiments 60-64, wherein the blood flow at an ischemic tissue of said subject is blocked for 2 minutes.

66. The method of any of embodiments 64-65, wherein said blood flow is blocked by an inflatable balloon.

67. The method of embodiment 66, wherein said balloon is inflated to block at least 80% of blood flow distal to said balloon.

68. The method of any of embodiments 60-67, wherein said composition is provided to said subject at a rate of no more than 2.5 mL per minute.

69. The method of any of embodiments 60-68, wherein said composition provided to said subject is not subjected to a maximum shear of more than 9101/second.

70. The method of any of embodiments 60-69, wherein said composition is provided to said subject through a catheter having a lumen size of approximately 0.36 mm.

71. The method of any of embodiments 60-70, wherein said composition is provided to said subject at a dose of 5 mL per dose.

72. The method of any of embodiments 60-70, wherein said composition is provided under a set of parameter conditions not exceeding those of Parameter Set 1 of Table 2.

73. The method of any of embodiments 60-70, wherein said composition is provided under a set of parameter conditions not exceeding those of Parameter Set 2 of Table 2.

74. The method of any of embodiments 60-70, wherein said composition is provided under a set of parameter conditions not exceeding those of Parameter Set 3 of Table 2.

75. The method of any of embodiments 60-70, wherein said composition is provided under a set of parameter conditions not exceeding those of Parameter Set 4 of Table 2.

76. The method of any of embodiments 60-70, wherein said composition is provided under a set of parameter conditions not exceeding those of Parameter Set 5 of Table 2.

77. The method of any of embodiments 60-70, wherein said composition is provided under a set of parameter conditions not exceeding those of Parameter Set 6 of Table 2.

78. The method of any of embodiments 60-71, wherein said composition is provided as a single dose.

79. The method of any of embodiments 60-71, wherein said composition is provided as at least two doses.

80. The method of any of embodiments 60-71, wherein said composition is provided as four doses of 5 mL each.

81. The method of any of embodiments 60-71, wherein said composition is provided as a single dose per day on each of multiple days.

82. The method of any of embodiments 60-71, wherein said composition is provided as at least two dose per day on each of multiple days.

83. The method of any of embodiments 60-82, wherein providing to said subject a composition is followed by a resting period of not more than 5 minutes following each dose provided.

84. The method of any of embodiments 60-82, wherein providing to said subject a composition is followed by a resting period of not more than 4 minutes following each dose provided.

85. The method of any of embodiments 60-82, wherein providing to said subject a composition is followed by a resting period of not more than 3 minutes following each dose provided.

86. The method of any of embodiments 60-82, wherein providing to said subject a composition is followed by a resting period of not more than 2 minutes following each dose provided.

87. The method of any of embodiments 60-82, wherein providing to said subject a composition is followed by a resting period of not more than 1 minute following each dose provided.

88. The method of any of embodiments 83-87, wherein a last resting period is followed by a 3 mL dose of a chaser solution to evacuate any remaining cells at a rate not exceeding 2.5 mL per minute.

89. The method of any of embodiments 60-86, wherein said composition is provided intravascularly.

90. The method of any of embodiments 60-86, wherein said composition is provided intramuscularly.

91. The method of any of embodiments 60-86, wherein said composition is provided intra-arterially.

92. The method of any of embodiments 60-86, wherein said composition is provided intra-coronarily.

93. The method of any of embodiments 60-92, wherein said composition is provided using a catheter coated with a biocompatible material.

94. The method of any of embodiments 60-93, wherein said composition comprises any of the compositions of embodiments 1-34.

95. The method of any of embodiments 60-93, wherein said composition comprises any of the regenerative cell compositions made by the methods of embodiments 38-61.

96. The method of any of embodiments 60-95, wherein the ischemia is cardiac ischemia.

97. The method of any of embodiments 60-95, wherein the ischemia is critical limb ischemia.

DETAILED DESCRIPTION

Aspects of the embodiments disclosed herein include methods of making cell populations that are significantly improved over conventional cell populations for amelioration or improvement of ischemic conditions (e.g., cardiac ischemia, limb ischemia). Particular formulations of cell populations and methods of use thereof have been generated, which unexpectedly improve ischemic conditions (e.g., greater than 4-fold improvement in left ventricle ejection fraction (LVEF) after cardiac ischemia, as compared to conventional approaches, and greater than 25% improvement in amputation-free survival rate after critical limb ischemia). It has been discovered that conventional cell populations having stem and progenitor cells do not have an appropriate viscosity, and/or anticoagulant, and are not delivered to the subject in a manner that improves or promotes cell viability. Accordingly, aspects of the invention relate to compositions comprising a first cell population that comprises bone marrow stem and progenitor cells, and anticoagulant, and an aqueous buffer and/or an autologous serum and/or an autologous plasma fraction, wherein the composition has a viscosity of not more than 5.0 centipose (cP) measured at 37° C., and methods of delivery such that the composition is provided to a subject at a rate of not more than 2.5 mL/minute.

Aspects of the embodiments disclosed herein include methods for bone marrow aspiration, which comprise a) preparation of bivalirudin solution, b) filling of syringes with anticoagulant solution, and c) aspiration of bone marrow into the syringe containing the said anticoagulant solution. The said method for bone-marrow harvesting and processing, further comprises an amount of an anticoagulant, which minimizes clot formation up to 90 minutes without affecting the efficacy of stem cell therapy and minimizing adverse pen-procedure bleeding or clotting events. Another important aspect of some embodiments is the avoidance of using any xenobiotic or citrate agents in the processing of bone marrow.

Aspects of the embodiments disclosed herein include compositions comprising bone marrow stem cells and/or progenitor cells. In some contexts, with respect to particular embodiments, the phrase 'bone marrow stem cells and/or progenitor cells' is meant to encompass bone marrow cell populations that may differentiate into a specific cell type, independent of whether they may replicate indefinitely or not, and/or produce growth factors, and/or facilitate, contribute, or promote blood vessel formation, an increase in blood vessel diameter, and/or an increase in blood flow in a tissue (e.g., an ischemic tissue).

Yet more embodiments concern the rapid analysis and an improved technique for bone marrow processing thereby yielding a defined mixture of desired cellular product, and if required the addition of plasma as a diluent, within limits of the intended dosage and viscosity. The initial cell count of harvested bone marrow and processed cellular product would be rapidly performed at the patient's bedside. The said mixture of cellular product comprises, but not limited to, Hematopoietic stem cells (HSC) and/or Hematopoietic progenitor cells (HPC) and/or CD34 positive cells, identified following ISHAGE guidelines for CD34 positive cell enumeration; Mesenchymal stem cells (MSC) and/or stromal cells, identified as at least lineage negative/dim, CD45 negative/dim and CD73 positive cells; Endothelial progenitor cells (EPC), identified as at least CD45 negative/dim, CD34 positive and vascular endothelial growth factor receptor 2 (VEGFR2) positive cells; CXCR4 progenitor cells identified as at least lineage negative/dim, CD45 negative/dim, and CD184 (CXCR4) positive cells. The said mixture of progenitor cells should also possess colony forming capacity as assessed by colony forming unit assays for HSC/HPCs, MSCs/stromal cells and EPCs. The aforementioned cell population comprises a variety of cell types that work synergistically in the overall healing of the injured tissue.

Along with the composition, the dosage and dosing method of the stem cells infusion are embodiments. A rapid testing of the cellular mixture is performed in a point-of-care environment, ensuring a range of $10^7$ to $10^9$ Mononuclear cells (MNC), including HSC not less than $10^4$ per dose, MSC not less than $5\times10^2$ per dose, EPC not less than $5\times10^2$ per dose, CXCR4 positive cells not less than $5\times10^3$ per dose and a final viscosity measured at 60° Fahrenheit to 98.6° Fahrenheit and delivered at normal body temperature between 1.0 to 5.0 centipoise (cP) as titrated with autologous PLASMA in the cellular product. The mode of administration of the processed cellular mixture is further infused intramuscularly and/or intravascularly at a rate of 0.5 mL to 2.5 mL per minute, as an adjuvant therapy. The said intravascular route further comprises intra-arterial such as intra-coronary by employing a catheter having at least two independent lumens one of which delivers the cells and is coated with a biocompatible or bioinert polymer having an inner diameter between 0.012" to 0.019" and the other lumen for inflating a polymeric balloon for restricting blood flow; intra-venous; and the intramuscular mode of administration comprises intra-myocardial, intra-epicardial, intra-muscular and so on.

The source material for the compositions and methods disclosed herein may be bone marrow. Other stem cell sources are contemplated. The bone marrow from which stem cells are isolated can be selected from the group comprising iliac crest, femora, tibiae, sternum, spine, ribs or other medullary spaces in bone. A preferred bone marrow source is the iliac crest. In some embodiments the stem and/or progenitor cell source such as the bone marrow stem cell source is autologous to the patient who will ultimately receive the composition. In some embodiments, before starting the aspiration of bone marrow, the anticoagulant solution is filled into aspiration syringes. A number of anticoagulant sources are contemplated, for example a coumarin, a vitamin K antagonist, an indirect thrombin inhibitor, heparin, a factor Xa inhibitor, a direct thrombin inhibitor, batroxobin, hemetin, a purified plant extract, EDTA, citrate, oxalate, and a nitrophorin. A preferred anticoagulant is bivalirudin.

Bivalirudin has a number of beneficial properties, such as a short (20 minute) half-life and a mode of action which is independent of many other anticoagulants, such as heparin, which may be independently administered to the patient pursuant to surgical intervention through which stem cell sources such as bone marrow sources are obtained. In some embodiments the concentration of anticoagulant, such as bivalirudin, to be used is 0.9 mg/mL, 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 24 mg/mL, 25 mg/mL, 26 mg/mL, 27 mg/mL, 28 mg/mL, 29 mg/mL, 30 mg/mL, 31 mg/mL, 32 mg/mL, 33 mg/mL, 34 mg/mL, 35 mg/mL, 36 mg/mL, 37 mg/mL, 38 mg/mL, 39 mg/mL, 40 mg/mL, 41 mg/mL, 42 mg/mL, 43 mg/mL, 44 mg/mL, 45 mg/mL, 46 mg/mL, 47 mg/mL, 48 mg/mL, 49 mg/mL, 50 mg/mL, 51 mg/mL, 52 mg/mL, 53 mg/mL, 54 mg/mL, or 55 mg/mL. In some embodiments the concentration of anticoagulant, such as bivalirudin, to be used falls in the range of 1 mg/mL to 50 mg/mL, preferably 5 mg/mL to 35 mg/mL, more preferably 10 mg/mL to 25 mg/mL, most preferably 20 mg/mL. Illustratively, each vial may contain 250 mg of bivalirudin, to which 5 mL of sterile water is added for injection. One may gently swirl the anticoagulant such as bivalirudin with the water, for example until all material is dissolved and the solution appears clear. One may then aspirate the solution into a sterile syringe such as a 20 mL sterile syringe. One may then fill the syringe with 0.9% Sterile sodium chloride, for example, for injection up until 12.5 mL mark, to yield a final concentration of 20 mg/mL. One may then take three sterile 20 mL syringes and fill 2 mL of 20 mg/mL bivalirudin solution. One may then aspirate 18 mL of stem cell source in each syringe to make a final volume of 20 mL. The final concentration of the anticoagulant, such as bivalirudin, along with aspirated bone marrow, in each syringe may be 2 mg/mL. It is known to those skilled in the art of aspiration of bone marrow that the aspiration needle used is 7, 8, 9, 10, 11, 12, 13, 14, or 15 gauges, such as in the range of 8 to 14 gauges, such as such as in the range of 9 to 12 gauges, preferably the needle/trocar is of 11 gauges. The stem and/or progenitor cell source, such as bone marrow is aspirated in the syringe or syringes prefilled with anticoagulant solution, for example for a final cumulative volume between 120 mL to 180 mL. The aspiration syringe used may have a volume of 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 21 mL, 22 mL, 23 mL, 24 mL, 25 mL, 26 mL, 27 mL, 28 mL, 29 mL, 30 mL, 31 mL, 32 mL, 33 mL, 34 mL, 35 mL, 36 mL, 37 mL, 38 mL, 39 mL, 40 mL, 41 mL, 42 mL, 43 mL, 44 mL, 45 mL, 46 mL, 47 mL, 48 mL, 49 mL, 50 mL, 51 mL, 52 mL, 53 mL, 54 mL, 55 mL, 56 mL, 57 mL, 58 mL, 59 mL, 60 mL, 61 mL, 62 mL, 63 mL, 64 mL, 65 mL, 66 mL, 67 mL, 68 mL, 69 mL, 70 mL, 71 mL, 72 mL, 73 mL, 74 mL, 75 mL, 76 mL, 77 mL, 78 mL, 79 mL, 80 mL, 81 mL, 82 mL, 83 mL, 84 mL, 85 mL, 86 mL, 87 mL, 88 mL, 89 mL, 90 mL, 91 mL, 92 mL, 93 mL, 94 mL, 95 mL, 96 mL, 97 mL, 98 mL, 99 mL, 100 mL, 101 mL, 102 mL, 103 mL, 104 mL, 105 mL, 106 mL, 107 mL, 108 mL, 109 mL, or 110 mL, preferably may fall in the range of 5 mL to 100 mL, preferably 10 to 60 mL, more preferably 20 to 50 mL, most preferably 20 mL.

Modifications to the above method may be made without departing from the invention. For example, entry may be made into more than one-site to aspirate bone marrow. Some amount of anti-coagulant solution may be injected into bone marrow before aspirating it. In the next step, the aspirated bone marrow is thoroughly mixed with anticoagulant solution by rolling gently between the palms of hands. The bone marrow is then transferred into a device for separating the components of bone marrow, the art of which is known.

The stem and/or progenitor cell source, such as bone marrow, may be removed from the patient or subject, for example by aspiration or excision. In a preferred embodiment, the stem cell source, such as bone marrow, is removed via aspiration. The stem cell source, such as bone marrow, for example aspirated bone marrow, may be autologous, and may be analyzed (both at pre- and post-processing step) and processed, in a point-of-care environment. As an example of removal and examination at a point-of-care environment, initially 120 mL of anti-coagulated bone-marrow is harvested. Nucleated cells present per ml of sample are rapidly analyzed using a small sample (less than 0.5 mL) of it. If needed 30-60 mL of additional bone marrow sample is harvested for processing in order to get the desired infusion cell dose. In some embodiments the processing technology comprises the following components; (i) a single sterile, disposable bone marrow processing device that can process variable volumes of bone-marrow up to 200 mL, (ii) a control module having at least one gravitational and one or more Infra-red (IR)/optical sensors coupled with a microprocessor and motors that control the flow, movement, and compartmentalization of the separated fractions into a disposable device or compartment, (iii) a docking station for the control module that transfers processing data from the control module firmware to a computer and (iv) a centrifuge with programmable parameters. In some embodiments, the purification device comprises at least one of the components recited above. Through practice of the methods herein, one may isolate stem and progenitor cells from bone marrow, so as to produce at least one of a stem cell fraction, a plasma fraction, and a red blood cell fraction, preferably in less than 30 minutes at the patient's bedside, which may also serve as the source of the autologous plasma. In some embodiments, a stem cell fraction, plasma fraction, and a red blood cell fraction may differ in their viscosities. In some embodiments, a stem cell fraction may have a viscosity of above 5.0 cP at 37° C., and a plasma may have a viscosity of below 5.0 cP at 37° C., such as substantially below 5.0 cP at 37° C., such that one may in some embodiments add a volume of the plasma to the stem cell fraction having a viscosity of above 5.0 cP at 37° C., such that the composition comprising the stem cell fraction a volume of the plasma may have a viscosity of 5.0 cP or lower at 37° C. As beneficially disclosed herein, the concentrated stem cells infusate (BM-$C_E$PC) viscosity is titrated to ensure shear stresses are controlled during trans-catheter delivery. A viscometer, possibly including but not required ancillary software, may be used to determine the stem cell concentrate viscosity in units (for example, centipoise (cP)), and to calculate the required plasma volume required to yield a final infusate in a preferred range of 1.8-5 cP at 98.6° Fahrenheit or 37° Celsius. A preferred infusate viscosity is 3.1 cP-5.0 cP, and a most preferred infusate viscosity is 1.8 cP-3.0 cP, and a most preferred infusate viscosity is 2.0 cP to 2.5 cP, and anything beyond 5.0 cP is not preferred. In some embodiments, the infusate viscosity is less than or equal to or any number in between 1.8 cP, 1.9 cP, 2.0 cP, 2.1 cP, 2.2 cP, 2.3 cP, 2.4 cP, 2.5 cP, 2.6 cP, 2.7 2.8 cP, 2.9 cP, 3.0 cP, 3.1 cP, 3.2 cP, 3.3 cP, 3.4 cP, 3.5 cP, 3.6 cP, 3.7 cP, 3.8 cP, 3.9 cP, 4.0 cP, 4.1 cP, 4.2 cP, 4.3 cP, 4.4 cP, 4.5 cP, 4.6 cP, 4.7 cP, 4.8 cP, 4.9 cP, or 5.0 cP.

The stem cell source, such as bone marrow, may be stratified using a device such as a disposable centrifugal cell stratification device, which may have controlled valving capable of responding to motor driven on and off positioning and may have a density functioning separation device such that bone marrow derived cell populations above or below the device may be harvested, although variations on each parameter of a device consistent with the parameters mentioned above, and alternatives comprising the use of alternative devices or for which cells are stratified without the use of a device as disclosed herein are also contemplated. Some embodiments comprise an optional on-board firmware for controlling the interrogation and harvest of certain cell populations within a multi-stratified zone driven by differences in a light source transmission value responding to pre-determined light units or an equivalency density separation device whose density equals the targeted cells density to mass ratio, a rapid analytical instrument verifying certain cell populations or cell dose and viscosity of certain populations, and an intravascularly placed balloon catheter where said balloon is inflated proximally to the target organ for a specified period stopping 80-100% blood flow to induce ischemia. In some embodiments, the controlled minimal cell shearing infusion of harvested cells and factors through the cannula lumen at a rate of 0.5 mL to 2.5 mL per minute as controlled or metered by a device, such as a mechanical pump or hand controlled method, as interpreted by an in-line manual pressure meter results in a reduced degree of apoptosis or other cell death. In some embodiments, cell fractionation is beneficially attained upon fractionation at 2000×g high speed spin for 15 minutes, followed by 80×g low speed spin for five minutes, or variants thereupon, such as a first spin of 5, 6, 7, 8, 9, 10, 11, 12, 13, 14, 15, 16, 17, 18, 19 or 20 minutes, a first g-force of 1500, 1600, 1700, 1800, 1900, 2000, 2100, 2200, 2300, 2400, or 2500, a second spin for 1, 2, 3, 4, 5, 6, 7, 8, 9, or 10 minutes at a g-force of 40, 50, 60, 70, 80, 90, 100, 110, 120, 130, 140, 150, or 160.

The composition generated hereby, such as a cell population comprising bone marrow stem cells, for example an aspirated and processed bone marrow-derived stem cell population, may be infused as an adjuvant to primary care, such as primary care in response to ischemia (e.g., cardiac ischemia and/or limb ischemia). The stem cell composition concentrate, for example an aspirated and processed bone marrow-derived stem and progenitor cell population, with or without factors, is infused, in some embodiments, shortly after the tissue becomes ischemic. In some embodiments the stem cell composition concentrate, for example an aspirated and processed bone marrow-derived stem cell population, with or without factors, is infused after ischemic conditioning of the tissue. In some embodiments, ischemic conditioning is effected by obstructing such as stopping blood flow to the affected area, for example using an over the wire inflatable balloon inflated to reduce blood flow, or other reversibly active obstructant of blood flow to obstruct or impede blood flow distally to the balloon. In preferred embodiments the obstructant such as a wire guided inflated balloon obstructs 80-99.99% of blood flow, such as greater than or equal to any number in between 80%, 81%, 82%, 83%, 84%, 85%, 86%, 87%, 88%, 89%, 90%, 91%, 92%, 93%, 94%, 95%, 96%, 97%, 98%, or 99%, or greater than 99%, or for a period of no more than three minutes, preferably one minute and most preferred for two minutes. Following a short period of tissue ischemia such as period of no more than three minutes, preferably one minute and most preferred for two minutes, cells are infused at a controlled rate, no more than 2.5 mL per minute, such as 0.5 mL per minute, 0.6 mL per minute, 0.7 mL per minute, 0.8 mL per minute, 0.9 mL per minute, 1.0 mL per minute, 1.1 mL per minute, 1.2 mL per minute, 1.3 mL per minute, 1.4 mL per minute, 1.5 mL per minute, 1.6 mL per minute, 1.7 mL per minute, 1.8 mL per minute, 1.9 mL per minute, 2.0 mL per minute, 2.1 mL per minute, 2.2 mL per minute, 2.3 mL per minute, 2.4 mL per minute, or up to 2.5 mL per minute.

It is beneficially disclosed that infusion at a high shear rate may induce apoptosis/cell death in a substantial fraction of the composition generated hereby, such as a stem cell composition, for example an aspirated and processed bone marrow-derived stem and/or progenitor cell population. Accordingly, in some embodiments a shear rate of 9101/second is an upper limit for the shear to which cells are exposed. Shear rate is a function of catheter diameter, and flow rate. Beneficially disclosed herein is the observation that a catheter with a approximately 0.36 mm, or 0.014" diameter and length of 1550 mm at a maximum shear rate of 9101/second should not exceed infusion above 2.5 mL/min with a bone marrow viscosity of 5 cP. Alternately, at a viscosity of approximately 4 cps at the preferred flow rate of 2.5 mL/min one may observe a loss, for example through apoptosis or other cell death, of 40% of the MNCs one hour post-infusion. Accordingly, a beneficial set of parameters for the infusion of a composition generated hereby, such as a stem cell composition, for example an aspirated and processed bone marrow-derived stem and progenitor cell population, used is infused as an adjuvant to primary care, such as primary care in response to ischemia, may comprise a composition viscosity from 1.6 to 5 cP, flow rate of 0.5 mL to 2.5 mL/min, lumen size approximately 0.36 mm and using a 5 mL syringe we could hold the psi to 3.4 to 44.64 with a plunger pressure of 0.58 lbf to 25.0 lbf and minimize the apoptosis or other cell death in said composition. It is observed using manual delivery of infusate with higher-viscosity compositions may be more sensitive to the application of variable plunger forces. Accordingly, in some embodiments use of a 5 mL syringe is preferred as in some embodiments it may lower the force required for a given pressure compared to syringes of larger volume and in some embodiments may be beneficial, for example ergonomically beneficial, for promoting more consistent control of the delivery rate.

A study of the impact of flow rate, viscosity, pressure, syringe size and plunger force on shear rate is given in Table 1, below.

TABLE 1

| S. no. | Lumen Inner diameter (mm) | Flow rate (mL/min) | Flow rate (uL/sec) | Wall Shear rate (WSR)/second | Wall Shear Stress (dyne/cm2) | Fluid viscosity (centapoise, cP) | Pressure (psi) | Plunger force (lbf) 5 mL syringe | Plunger force (lbf) 10 mL syringe | Plunger force (lbf) 20 mL syringe |
|---|---|---|---|---|---|---|---|---|---|---|
| 1 | 0.36 | 1 | 16.667 | 3640 | 72.81 | 2 | 8.928 | 1.526688 | 2.258784 | 3.919392 |
| 2 | 0.36 | 1.25 | 20.83375 | 4550 | 91.013 | 2 | 11.16 | 1.90836 | 2.82348 | 4.89924 |
| 3 | 0.36 | 1.5 | 25.0005 | 5460 | 109.215 | 2 | 13.392 | 2.290032 | 3.388176 | 5.879088 |
| 4 | 0.36 | 1.75 | 29.16725 | 6370 | 127.418 | 2 | 15.624 | 2.671704 | 3.952872 | 6.858936 |
| 5 | 0.36 | 2 | 33.334 | 7281 | 145.62 | 2 | 17.856 | 3.053376 | 4.517568 | 7.838784 |
| 6 | 0.36 | 2.25 | 37.50075 | 8191 | 163.823 | 2 | 20.088 | 3.435048 | 5.082264 | 8.818632 |
| 7 | 0.36 | 2.5 | 41.6675 | 9101 | 182.025 | 2 | 22.32 | 3.81672 | 5.64696 | 9.79848 |
| 8 | 0.36 | 2.75 | 45.83425 | 10011 | 200.228 | 2 | 24.552 | 4.198392 | 6.211656 | 10.77833 |
| 9 | 0.36 | 3 | 50.001 | 10921 | 218.43 | 2 | 26.784 | 4.580064 | 6.776352 | 11.75818 |
| 10 | 0.36 | 3.25 | 54.16775 | 11831 | 236.633 | 2 | 29.016 | 4.961736 | 7.341048 | 12.73802 |

For a given maximum shear of 9101/second, a range of viscosities, pressures, syringe sizes and plunger forces are given in Table 2, below.

TABLE 2

| Parameter Set | Viscosity (cP) | Pressure (Psi) | Syringe size (mL) | Plunger force (lbf) |
|---|---|---|---|---|
| 1 | 2 | 22.32 | 5 | 3.81672 |
| 2 | 4 | 44.64 | 5 | 7.63344 |
| 3 | 2 | 22.32 | 10 | 5.64696 |
| 4 | 4 | 44.64 | 10 | 11.29392 |
| 5 | 2 | 22.32 | 20 | 9.79848 |
| 6 | 4 | 44.64 | 20 | 19.59696 |

Impact of different flow rates and viscosities on the cell health and potency are given in Table 3, below.

TABLE 3

| Sample type | % Live Cells | Dead and Apoptotic cells (%)-Annexin-V Assay | % Cell Viability (7AAD/PI) | Average Pressure (Psi) | Viscosity (cP) | % Change in MNC counts 1 h post-incubation | % Change in Colony forming units (CFUs) |
|---|---|---|---|---|---|---|---|
| Pre-processed (untreated cells) | 90.30 | 9.70 | 94.02 | — | 1.6-1.8 | — | — |
| VXP processed | 83.50 | 16.50 | 94.4 | — | 1.6-1.8 | Baseline | — |
| Post-Catheter (1 mL/min) | 79.60 | 20.40 | 95.35 | 6.8 | 1.6-1.8 | No change | — |
| Post-Catheter (2.5 mL/min) | 75.2 | 24.8 | 95.02 | 20 | 1.6-1.8 | −10.08 | — |
| | | | | 26.1 | 3.1-5.0 | | −17.43 |
| Post-Catheter (5 mL/min) | 75.70 | 24.30 | 91.3 | 42 | 1.6-1.8 | −33.92 | — |

In some embodiments the pressure applied is less than or equal to or any number in between 15 psi, 16 psi, 17 psi, 18 psi, 19 psi, 20 psi, 21 psi, 22 psi, 23 psi, 24 psi, 25 psi, 26 psi, 27 psi, 28 psi, 29 psi, 30 psi, 31 psi, 32 psi, 33 psi, 34 psi, 35 psi, 36 psi, 37 psi, 38 psi, 39 psi, 40 psi, 41 psi, 42 psi, 43 psi, 44 psi, 45 psi, 46 psi, 47 psi, 48 psi, 49 psi, 50 psi, 51 psi, 52 psi, 53 psi, 54 psi, 55 psi, 56 psi, 57 psi, 58 psi, 59 psi, or 60 psi.

In some embodiments the plunger force is less than or equal to or any number in between 4 lbf, 5 lbf, 6 lbf, 7 lbf, 8 lbf, 9 lbf, 10 lbf, 11 lbf, 12 lbf, 13 lbf, 14 lbf, 15 lbf, 16 lbf, 17 lbf, 18 lbf, 19 lbf, 20 lbf, 21 lbf, 22 lbf, 23 lbf, 24 lbf, or 25 lbf.

The infusion is done intravascularly and/or intramuscularly. Preferred infusion is intravascular, more preferably intra-arterial most preferably intra-coronary using a catheter coated with a biocompatible material. The intracoronary delivery may be in a single dose or multiple doses or a single dose on different days or a multiple dose on different days. Doses are beneficially administered for not more than two minutes to prevent further ischemic damage, and may each be followed by a resting period during which the infusion site is exposed to blood flow, such as a resting period of 1, 2, 3, 4, or 5 minutes, and doses may be delivered singly, or two at a time, three at a time, four at a time, or more than four at a time, consecutively at an administration period, which may be followed by 3 mL of chaser solution, in some embodiments not exceeding 2.5 mL/min flow rate, to evacuate any remaining cells from the catheter lumen, and which may constitute a single administration period or may be repeated at multiple administration periods such as administration periods on successive days, or separated by 1, 2, 3, 4, 5, 6, 7, or more than 7 days. That is, one may administer one dose for not more than 2 minutes followed by a resting period of 1 minute, or one may administer one dose for not more than 2 minutes followed by a resting period of 2 minutes, or one may administer one dose for not more than 2 minutes followed by a resting period of 3 minutes, or one may administer one dose for not more than 2 minutes followed by a resting period of 4 minutes, or one may administer one dose for not more than 2 minutes followed by a resting period of 5 minutes, or one may administer two doses for not more than 2 minutes each followed by a resting period of 1 minute, or one may administer two doses for not more than 2 minutes each followed by a resting period of 2 minutes, or one may administer two doses for not more than 2 minutes each followed by a resting period of 3 minutes, or one may administer two doses for not more than 2 minutes each followed by a resting period of 4 minutes, or one may administer two doses for not more than 2 minutes each followed by a resting period of 5 minutes, or one may administer three doses for not more than 2 minutes each followed by a resting period of 1 minute, or one may administer three doses for not more than 2 minutes each followed by a resting period of 2 minutes, or one may administer three doses for not more than 2 minutes each followed by a resting period of 3 minutes, or one may administer three doses for not more than 2 minutes each followed by a resting period of 4 minutes, or one may administer three doses for not more than 2 minutes each followed by a resting period of 5 minutes, or one may administer four doses for not more than 2 minutes each followed by a resting period of 1 minute, or one may administer four doses for not more than 2 minutes each followed by a resting period of 2 minutes, or one may administer four doses for not more than 2 minutes each followed by a resting period of 3 minutes, or one may administer four doses for not more than 2 minutes each followed by a resting period of 4 minutes, or one may administer four doses for not more than 2 minutes each followed by a resting period of 5 minutes, and the total administration may be followed by 1 mL, 2 mL, 3 mL or more than 3 mL of chaser solution to evacuate any remaining cells from the catheter lumen in a single administration period.

For illustration, 4 doses of 5 mL each (total 20 ml) cellular product may infused at 2.5 mL per minute, followed by a resting period of 1-5 minutes, over a period of 12 to 28 min combined, followed by 3 mL of chaser solution infused at 2.5 mL per minute to evacuate any remaining cells from the catheter lumen in a single administration period.

In a first set of human clinical trials, it was found that a significantly improved response after cardiac ischemia could be obtained using the formulations of cell populations described herein. Improvement after cardiac ischemia is clinically measured by observing an improvement in LVEF. A cell population comprising bone-marrow-derived stem cells was prepared as described herein having a viscosity of less than or equal to or anything in between 1.0 cP through 5.0 cP (e.g., 1.0 cP, 1.5 cP, 2.0 cP, 2.5 cP, 3.0 cP, 3.5 cP, 4.0 cP, 4.5 cP, or 5.0 cP or anywhere in between). The cell population was produced through a method of making a regenerative cell composition comprising: (a) providing a first cell population that comprises bone marrow stem cells; (b) mixing an anticoagulant with said first cell population so as to produce a composition comprising said first cell population and anticoagulant; (c) enriching bone marrow stem cells within said composition comprising said cell population and anticoagulant so as to produce a second cell population that comprises enriched bone marrow stem cells; (d) isolating a fraction comprising said second cell population that comprises enriched bone marrow stem cells; and (e) adjusting the viscosity of said fraction using a liquid to a viscosity of not more than 5.0 cP measured at 37° C. so as to make said regenerative cell composition. This formulation was provided to patients suffering from cardiac ischemia by catheter at a flow-rate of less than 2.5 mL/min (e.g., a number less than or equal to or in between 0.5 mL/min, 1.0 mL/min, 1.5 mL/min, 2.0 mL/min, or 2.5 mL/min). The LVEF of the patient was determined over time and it was found that the provision of the cell population comprising bone marrow-derived stem cells prepared as described herein provided a 4-fold improvement of LVEF as compared to conventional bone marrow-derived stem cell populations (see, for a survey of conventional stem cell composition performance, Delewi et al., (2013), "Impact of intracoronary bone marrow cell therapy on left ventricular function in the setting of ST-segment elevation myocardial infarction: a collaborative meta-analysis" European Heart Journal, 2013 Sep. 11, doi:10.1093/eurheartj/eht372).

In a second set of human clinical trials, it was found that a significantly improved response after critical limb ischemia could be obtained using the formulations of cell populations described herein. Improvements of critical limb ischemia is clinically measured by observing an improvement in amputation-free survival rate. A cell population comprising bone marrow-derived stem cells was prepared as described herein having a viscosity of less than or equal to or anything in between 1.0 cP through 5.0 cP (e.g., 1.0 cP, 1.5 cP, 2.0 cP, 2.5 cP, 3.0 cP, 3.5 cP, 4.0 cP, 4.5 cP, or 5.0 cP or anywhere in between). The cell population was produced through a method of making a regenerative cell composition comprising: (a) providing a first cell population that comprises bone marrow stem cells; (b) mixing an anticoagulant with said first cell population so as to produce a composition comprising said first cell population and anticoagulant; (c) enriching bone marrow stem cells within said composition comprising said cell population and anticoagulant so as to produce a second cell population that comprises enriched bone marrow stem cells; (d) isolating a fraction comprising said second cell population that comprises enriched bone marrow stem cells; and (e) adjusting the viscosity of said fraction using a liquid to a viscosity of not more than 5.0 cP measured at 37° C. so as to make said regenerative cell composition. This composition was provided to patients suffering from critical limb ischemia by cannula at a flow-rate of less than 2.5 mL/min (e.g., a number less than or equal to or in between 0.5 mL/min, 1.5 mL/min, 2.0 mL/min, or 2.5 mL/min). The amputation-free survival rate of the patients was determined over time and it was found that the provision of the cell population comprising the bone marrow-derived stem cells prepared as described herein provided a 25% improvement of amputation-free survival as compared to conventional bone marrow-derived stem cell populations as compared to studies including the Harvest Technologies CLI study, Therapeutic Angiogenesis using Cell Transplantation in critical limb ischemia (TACT study), and an Amann et al Study as listed at Example 6, below.

Thus, through the practice of the disclosure herein, one may observe dramatic improvements over results observed previously with conventional bone marrow-derived stem cell populations for the treatment of ischemia (e.g., cardiac ischemia and limb ischemia). One can observe in some instances a percent improvement in left ventricle ejection fraction (LVEF) of 2×, 3×, 4×, or 5×, or more than 5× as compared to a conventional preparation of a cell population comprising bone marrow stem cells. Similarly, one can observe in some instances a percent improvement in amputation free survival rate among limb ischemia patients of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or greater than 24% as compared to a conventional preparation and delivery of a cell population comprising bone marrow stem cells.

EXAMPLES

Example 1

Bone Marrow Aspiration

The bone marrow used as a source material was autologous. The bone marrow from which stem cells are isolated was selected from the group consisting of iliac crest, femora, tibiae, spine, and ribs, or other medullary spaces in bone. The preferred bone marrow source was the iliac crest. Before starting the aspiration of bone marrow, the anticoagulant solution was filled into aspiration syringes. Each vial contains 250 mg of bivalirudin. 5 ml of sterile water was added for injection and the vial was gently swirled until all material was dissolved. The solution was poured into a 20 ml sterile syringe. The syringe was filled with 0.9% sodium chloride for injection to the 12.5 ml mark, to yield a final concentration of 20 mg/ml. Next, three sterile 20 ml syringes were filled with 2 ml of 20 mg/ml bivalirudin solution. 18 ml of bone marrow were aspirated in each syringe to make a final volume of 20 ml. The final concentration of bivalirudin, along with aspirated bone marrow, in each syringe was 2 mg/ml. The aspiration needle/trocar used was 11 gauge. Bone marrow was aspirated in the syringe or syringes pre-filled with anticoagulant solution for a final cumulative volume between 120 ml to 180 ml. The aspiration syringe used was a 20 ml syringe.

Modifications to the above method may be made without departing from the invention. For example, entry may be made into more than one-site to aspirate bone marrow. Some amount of anti-coagulant solution may be injected into bone marrow before aspirating it. In the next step, the aspirated bone marrow is thoroughly mixed with anticoagulant solution by rolling gently between the palms of hands. The bone marrow is then transferred into a device for separating the components of bone marrow, the art of which is known.

Example 2

Bone Marrow Cell Analysis and Processing

The aspirated bone marrow was analyzed (both at pre- and post-processing step) and processed, in a point-of-care environment. Initially 120 ml of anti-coagulated bone-marrow was harvested. Nucleated cells present per ml of sample were rapidly analyzed using a small sample (less than 0.5 ml) of it. If needed, 30-60 ml of additional bone marrow may be harvested for processing in order to get the desired infusion cell dose. The processing technology comprises the following components; (i) a sterile, disposable bone marrow processing device that can process variable volumes of bone-marrow up to 400 mL, (ii) a control module having at least one gravitational and one or more Infra-red (IR)/optical sensors coupled with a microprocessor and motors that control the flow, movement, and compartmentalization of the separated fractions into a disposable device or compartment, (iii) a docking station for the control module that transfers processing data from the control module firmware to a computer and (iv) a centrifuge with programmable parameters.

Example 3

Bone Marrow Viscosity and Analysis

The concentrated stem cells infusate viscosity was titrated to ensure shear stresses are controlled during trans-catheter delivery. A viscometer, possibly including but not required ancillary software, determined the stem cell concentrate viscosity in units (for example centipoise), and calculated the required plasma volume required to yield a final infusate in the preferred range of 1.8-5 cP at 98.6° Fahrenheit or 37° Celsius. A preferred infusate viscosity was 3.1 cP-5.0 cP, and the most preferred infusate viscosity was 1.8 cP-3.0 cP, or 2.0 cP-2.5 cP. The automated or manual processing technology having produced the stem cell fraction, plasma fraction, and RBC fraction in less than 30 minutes at the patient's bedside served as the source of the autologous plasma.

Example 4

Protocol for Infusion of Cellular Product

The aspirated and processed bone marrow was infused as an adjuvant to primary care. The bone-marrow stem cell, with or without factors, concentrate was infused after ischemic conditioning of the tissue. The blood flow to the affected area was stopped using an over the wire inflatable balloon inflated to reduce blood flow distally to the balloon 80-99.99% for a period of no more than three minutes, preferably one minute and most preferred for two minutes. Following a short period of tissue ischemia, cells were infused at a controlled rate, no more than 2.5 ml per minute. The infusion was done intravascularly and/or intramuscularly. Preferred infusion is intravascular, more preferably intra-arterial most preferably intra-coronary using a catheter coated with a biocompatible material. The intracoronary delivery was in a single dose or multiple doses or a single dose on different days or a multiple dose on different days. For illustrations, 4 doses of 5 ml each (total 20 ml) cellular product was infused over a period of 12 to 28 min, followed by 3 ml of chaser solution to evacuate any remaining cells from the catheter lumen.

Example 5

Safety Study of Autologous Bone Marrow Concentrate Enriched in Progenitor Cells (BMCEPC) as an Adjuvant, in the Treatment of Acute Myocardial Infarction A 43 year old male, non-diabetic, normo-tensive, non-obese, smoker presented with a history of two hours of chest pain and symptomatic of an AMI into the emergency department. On admission, a 2 mm ST segment elevation in the anterior leads was observed, and AMI was further confirmed with biochemical blood tests. The patient's Left Ventricular Ejection Fraction, LVEF, was estimated to be around 35% by bedside 2D ECHO. Primary percutaneous coronary intervention (PCI) was performed using a routine technique, and a single drug-eluting stent was deployed in the proximal LAD with TIMI-3 grade flow results. Post-PCI, the patient's LVEF remained <40% at the 120 hour time-point as measured by multigated acquisition (MuGA) and ECHO, which met our inclusion criteria and is predictive of a higher than acceptable one year mortality rate. LVEF is one of the key indications of mortality rates post MI with a reduced LVEF being a risk factor for both sudden and non-sudden death, with the odds ratio for 1-year mortality after MI at 9.48 for patients with LVEF ≤30% compared with patients with LVEF >50%, 2.94 for patients with LVEF 30-40%, whereas the risk was not significantly increased in patients with LVEF 40-50%.

The patient was advised that he met the inclusion criteria for the AMIRST clinical trial program using his own (autologous) bone marrow stem cells. The clinical trial was registered with clinicaltrials.gov (NCT01536106) and was approved by the Institutional Ethics Committee (IEC) (IEC Approval # TIEC/2011/32/02) and Institutional Committee for Stem Cell Research (IC-SCRT). The Patient, Primary Investigator and Clinical Investigator concurred, and consent was obtained. On the sixth day post PTCA/stent implant, the patient was transferred to the heart catheterization laboratory, and the AMIRST (Acute Myocardial Infarction Rapid Stem cell Therapy) protocol was completed as disclosed in the summary and detailed description herein.

The entire procedure was completed within 90 minutes, taking 30 minutes longer than anticipated as the vascular surgeon trained for collecting the bone marrow was delayed. As a preliminary safety study prior to full subject enrollment, the patient was followed up for 24 months, and evaluated with standard diagnostic metrics. No major adverse cardiac events (MACE) including re-hospitalization were reported, demonstrating the safety of this adjuvant treatment. The patient's LVEF improved from 36% (Day 0) at the time of the AMIRST treatment to 60.3% at 24 months post-AMIRST intervention. It is noted that in this study MuGA was used as the enrollment measurement technique. Caution should be taken in comparing MuGA and MRI LVEF results; however the enrollment LVEF was confirmed via a secondary method i.e. ECHO and the 3-month and 24-months LVEF results were confirmed by the same radiology team.

Upon written consent, and within a maximum window of 10 days post MI, the patient was taken to the heart catheterization laboratory (operating room suite) on Day 6 post-PCI, mildly to moderately sedated using 0.2 mcg/kg of Fentanyl, and 120 mL of bone marrow was aspirated from the patient's iliac crest using an 11-gauge Jamshidi needle optimized for cell harvest. Careful bone marrow aspiration technique was employed to reduce peripheral blood contamination in the aspirate. Following the aspiration, the bone marrow was processed employing our proprietary point-of-care technology platform to produce bone marrow concentrate enriched in progenitor cells ($BMC_EPC$). The cellular product contained a total of $3.54 \times 10^8$ BMMNCs. A guide-wire was introduced into the femoral artery followed by a double lumen ultra-low profile PTA intracoronary catheter, and the patient had four separate induced ischemia/progenitor cell infusions using the "stop-flow" technique before the entire optimal dose of nucleated cells was distally delivered to the stent in the LAD. The complete process was accomplished in 90 minutes at patient's bedside. The patient's hematological and biochemical parameters are listed in Table 4.

TABLE 4

Clinical Laboratory Values Pre and Post BMCePC Therapy

| | Pre BMCePC Infusion Day-2 | Post BMCePC Infusion Day 0 |
|---|---|---|
| Hemaglobin (g/dL) | 13.5 | 13.8 |
| RBC Count (x10(6)/uL) | 4.84 | 4.92 |
| Platelet Count (x10(3)/mL) | 110 | 120 |
| Creatinine, Serum (mg/dL) | 0.8 | 0.9 |
| Urea Nitrogen (mg/dL) | 13 | 12 |
| Creatine Kinase, Serum | 106 | 188 |
| N-Terminal pro-B Type Natriuretic Peptide (pg/mL) | 731.3 | — |

There were no adverse events (AE) or serious adverse events (SAE) reported during the procedure. The patient remained hospitalized for telemetry an additional 24 hours post cell transplant, and released with standard cardiac therapeutics as listed in Table 5.

TABLE 5

Medications Prescribed on Discharge post BMCePC Therapy

| Drug | Dose | Frequency | Drug Class |
|---|---|---|---|
| Ecosprin | 150 mg | Oral, Once Daily | Anti-platelet |
| Deplatt | 75 mg | Oral, Twice Daily | Anti-platelet |
| Rosuvas | 20 mg | Oral, Once Daily | Statin |
| Pantacid | 40 mg | Oral, Once Daily | Dyspepsia |

The patient was scheduled for follow-up on 1, 2, 3, 6, 12 and 24 months to assess the primary endpoints of safety and the secondary endpoints of efficacy that includes MACE, LVEF, cardiac output, cardiac remodeling and quality of life assessments. The 12-month follow-up could not be completed due to non-availability of patient, but all other follow-up points were completed. No Major Adverse Cardiac Events (MACE) or re-hospitalization events were reported. The patient continued to follow a normal life, after 2 weeks post the AMIRST procedure. At the 1-month follow-up, HOLTER monitoring was performed for 23 hours and 6 minutes. No ventricular ectopics were observed, and the heart variability was normal. The slowest episode of bradycardia (HR 53 bpm, 1 min 13 sec) was observed at midnight and the fastest episode of tachycardia (HR 141 bpm, 1 min 2 sec) was observed in the afternoon. Cardiac imaging was performed at each follow-up. The cardiac chambers appeared normal with no signs of pericardial effusion.

Overall, the study demonstrated safety of the bone marrow aspiration, processing and infusion methodology as disclosed herein in an acute low LVEF infarct patient post PTCA. FIGS. 2A-D show cardiac MR images obtained 3- and 24-months post-BMC$_E$PC infusion. At the 24-month follow-up, the cardiac MR findings were summarized as "Basal and mid-cavity anterior and anteroseptal and apical anterior and septal and apex myocardial post contrast sub-endocardial <25% to 50% with a focal spec of 75% transmural hyper-enhancement, consistent with ischemic infarction."

The pre-BMC$_E$PC infusion cardiac MR imaging was performed on a different instrument than the 3- and 24-months post-BMC$_E$PC infusion. Therefore, an absolute quantitative equivalency measurement of LVEF between the pre-treatment and 3-months post treatment should be evaluated cautiously. Also, the MuGA and ECHO scan results have a level of user dependency, and each result should be cautiously interpreted.

Nevertheless, a considerable improvement in the LVEF has been noted over the study period and between 3-months and 24-months follow-up. Post BMC$_E$PC infusion, the LVEF improved from 36% (Day 0) at the time of the AMIRST treatment to 55.3% at 3 months post-AMIRST intervention, and further improved from 55.3% to 60.3% at 24 months post-AMIRST intervention, as shown in Table 6. That is, the patient showed a 67.5% increase from day 0 through 24 months. This degree of improvement is considered atypical for a patient having suffered an ST elevated myocardial infarction with an ejection fraction below 40% post reperfusion (stenting).

TABLE 6

Time Endpoints: Left Ventricular Ejection Fraction (LVEF) Values and Safety

| Measurement Time | Method | Value | MACE |
|---|---|---|---|
| Time 0 Days | 2D Echo | 36% | N/A |
| Time 6 Days | MuGA | <40% | N/A |
| Time 7 Days | IC Angiogram | <40% | None |
| Time 3 Months F/U | cMRI | 55.30% | None |
| Time 24 Months F/U | cMRI | 60.30% | None |

The cardiac output (volumetrics) also showed an improvement from 2.7 l/min to 3.4 l/min over the same period, and is a secondary endpoint. No reduction in scar size was observed with a heart mass of 115.5 gms and a scar mass of 11.5 gms (approximately 11%).

As previously disclosed (Delewi et al., 2013), "Impact of intracoronary bone marrow cell therapy on left ventricular function in the setting of ST-segment elevation myocardial infarction: a collaborative meta-analysis" European Heart Journal, 2013 Sep. 11, doi:10.1093/eurheartj/eht372), a meta-analysis of 16 studies including 1641 patients (984 cell therapy, 657 controls) reported that absolute improvement in LVEF was increased 2.55% among BMC-treated patients compared with controls: [95% confidence interval (CI) 1.83-3.26, p value of 0.001]. Cell therapy significantly reduced LVEDVI and LVESVI (23.17 mL/m2, 95% CI: 24.86 to 21.47, p=0.001; 22.60 mL/m2, 95% CI 23.84 to 21.35, p value of 0.001, respectively). Among patients under age 55, the absolute improvement in LVEF was increased to a slightly greater 3.38%, and among patients with baseline LVEF <40%, the absolute improvement in LVEF was increased again to a slightly greater 5.30%.

Accordingly, the 67.5% degree of improvement or 24.3 percentage points of improvement observed through practice of the disclosure herein is more than 4-fold greater than the 5.30% level of improvement expected for the under 55 age cohort with baseline LVEF <40% to which the study patient would be a member using conventional techniques that utilize cell populations having bone marrow stem cells.

Example 6

60 Minute Rapid Bedside Treatment Reduces Amputations in No-Option Limb Ischemia Patients Critical limb ischemia afflicts an estimated 2 million people combined in the United States, European Union and Indian sub-continent, and results in approximately 500,000 amputations each year. The overall prevalence (0.23%) and incidence (0.20%) in the United States increases with age and diabetes status, and 5 year mortality rate post limb amputation reaches nearly 50%.

A patient treatment protocol was completed as disclosed in the summary and detailed description herein. Heparin was used as an anti-coagulant. Phase Ib clinical trial safety and efficacy results treating no-option patients suffering from critical limb ischemia CLIRST (Critical Limb Ischemia Rapid Stem cell Therapy) treatment are presented. The trial achieved both its primary safety endpoint and secondary efficacy endpoints at 12 months having no serious adverse events determined to be related to the therapy, and achieving statistical significance in amputation free survival rates (82.4%), pain reduction (mean VAS score pre-therapy 7.8±0.97 and 12 month follow-up 0.2±0.58 on a scale of 0-10, p=0.0005), 6-minute walking distance (mean distance pre-therapy of 14.5 meters±37.57 and 12 month follow-up of 157 meters±100.92, p=0.0039), open wound healing (11 patients had gangrene with or without ulceration pre-treatment and all patients had neither gangrene nor ulceration at 12 month follow-up), and TcPO2 (transcutaneous oxygen pressure) levels (mean pre-therapy of 14.66±6.93 improved to 35.75±17.04, p=0.0032.

Figure 1:
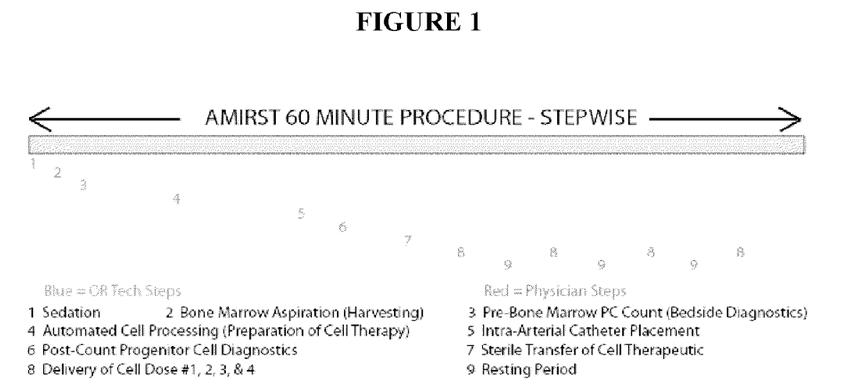
FIG. 1: Schematic representation of the treatment approach, achieving a desirable time frame for any bedside therapeutic in the heart catheterization procedure.
Figure 2A:
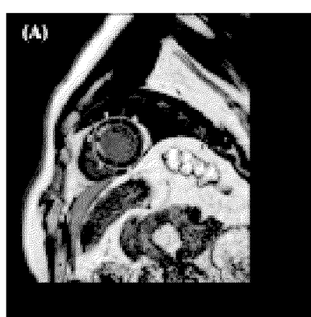
FIG. 2A: One section of the cardiac MR stacking used to calculate myocardial volume at 3 months post-$BMC_EPC$ infusion.
Figure 2B:
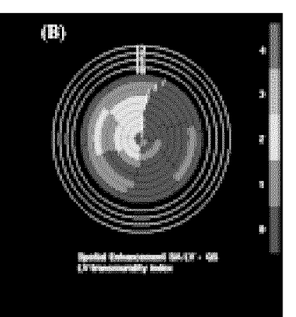
FIG. 2B: Left Ventricle transmurality index at 3 months post-$BMC_EPC$ infusion.
Figure 2C:
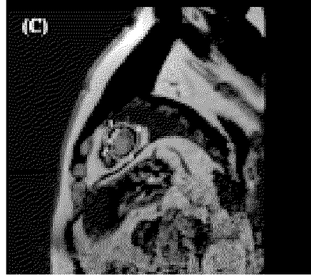
FIG. 2C: One section of the cardiac MR stacking used to calculate myocardial volume at 24 months post-$BMC_EPC$ infusion.
Figure 2D:
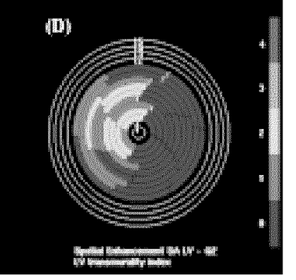
FIG. 2D: Left Ventricle transmurality index at 24 months post-$BMC_EPC$ infusion.
Figure 3A:
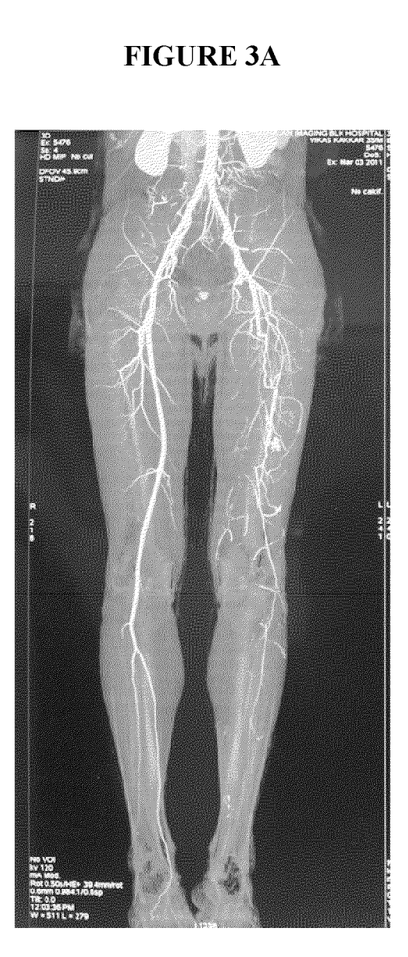
FIG. 3A: CT Angiogram (representative example) of a pre-treated (left leg) of subject number EHIRC/CLI-STEM-002 on enrollment in study demonstrating poor vascularity.
Figure 3B:
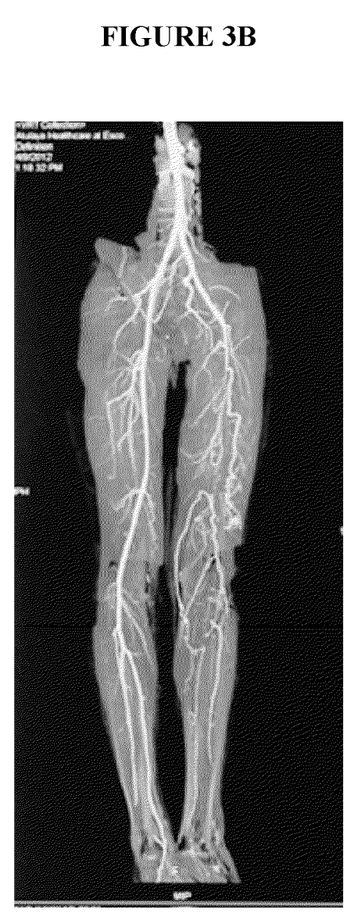
FIG. 3B: CT Angiogram (representative example) of 12 months post-treatment (left leg) of subject number EHIRC/CLI-STEM-002, demonstrating improvement of vascularity over FIG. 3A, above.

Additionally, and not demonstrated in earlier studies, vasculogenesis improvements in the treated leg were seen. Improvement was observed in both collateral vessel number (p=0.0156 in distal thigh, p=0.0313 in proximal leg), and vessel size (distal thigh, p=0.0156 and proximal leg, p=0.0625) were observed. FIGS. 3A and 3B depict images of improvement in collateral vessel size and number in an patent treated in this study.

Quantification of these results for a single exemplary individual is given in Table 7, presenting Qualitative and Quantitative collateral vessel data for subject EHIRC/CLI-STEM-002 as shown in pre and post angiograms, FIGS. 3A and 3B. An overview of aggregate results is given in Table 8, below, presenting data related to the number of collateral vessels and the collateral vessel size before and 12 months after administration of a composition herein through the practice of methods herein.

Categories used for the quantification were scored as follows: Category Scoring (No. of collateral Vessels): 0: No collateral vessels; 1: 1-3 Collateral vessels; 2: 4-7 Collateral Vessels; 3: =>8 Collateral Vessels; Grade Scoring (Size of Collateral Vessel): 0: No collateral vessels; 1: =<5 Small; 2: >5 Small; 3: =<5 large±Small; 4: >5 large±Small.

TABLE 7

| Vessel | Category (No. of Collaterals) | | | Grade (Size of Collateral Vessels) | | |
|---|---|---|---|---|---|---|
| | Pre-Intervention | Post-Intervention | p Value | Pre-Intervention | Post-Intervention | p Value |
| Proximal thigh | 0 | 0 | 0.1250 | 0 | 0 | 0.2500 |
| Mid thigh | 1 | 3 | 0.0547 | 1 | 3 | 0.1563 |
| Distal thigh | 1 | 3 | 0.0156 | 1 | 3 | 0.0156 |
| Proximal leg | 0 | 2 | 0.0313 | 0 | 3 | 0.0625 |
| Mid leg | 0 | 1 | 0.5000 | 0 | 1 | 0.7500 |
| Distal leg | 0 | 0 | >0.9999 | 0 | 0 | >0.9999 |

Table 8. Summary table of CT Angiography vessel collateral grading of 14 critical limb ischemia no-option patients (pre-intervention and 12 month post intervention) with the $BMC_EPC$ infusion intramuscularly.

| Parameters | | Number of Collateral Vessel Category | | | Size of Collateral Vessel Grade | | |
|---|---|---|---|---|---|---|---|
| | | Pre Mean (SD) | Post Mean (SD) | p Value | Pre Mean (SD) | Post Mean (SD) | p Value |
| Thigh | Proximal Thigh | 0.42 (0.793) | 0.75 (1.055) | 0.1250 | 0.58 (1.165) | 1.00 (1.348) | 0.2500 |
| | Mid Thigh | 0.58 (0.793) | 1.25 (1.357) | 0.0547 | 0.58 (0.793) | 1.17 (1.193) | 0.1563 |
| | Distal Thigh | 0.42 (0.669) | 1.42 (1.311) | 0.0156 | 0.33 (0.492) | 1.33 (1.155) | 0.0156 |
| Leg | Proximal Leg | 0.25 (0.622) | 1.08 (1.084) | 0.0313 | 0.17 (0.389) | 1.08 (1.165) | 0.0625 |
| | Mid Leg | 0.33 (0.778) | 0.67 (1.073) | 0.5000 | 0.25 (0.622) | 0.42 (0.669) | 0.7500 |
| | Distal Leg | 0.42 (0.996) | 0.42 (0.996) | >0.9999 | 0.25 (0.622) | 0.25 (0.622) | >0.9999 |

The open label single study enrolled 17 patients, of which 14 successfully achieved the 12 month major amputation free endpoint target. Patients were treated with a mean cell dose of $BMC_EPC$ (bone marrow concentrate enriched progenitor cells) of $8.04 \times 10^8$ ($\pm 3.65 \times 10^8$) cells in a 20 ml final product, which was injected intramuscularly in the lower afflicted leg. Additionally, patient participants in the study demonstrated an improved number of vessels in the mid-thigh (p=0.0547), distal thigh (p=0.0156); and proximal leg (p=0.0313), and improved vessel size in the distal thigh (p=0.0156), and proximal leg (p=0.0625).

A summary of amputation free survival rate 12 months post treatment with the $BMC_EPC$ infusion intramuscularly is given in Table 9, below.

TABLE 9

| | n (%) [N = 17] |
|---|---|
| Total Major Limb Amputation free survival rate | 14 (82.35) |
| Total Amputations | 5 (29.41) |
| Major Amputation | 3 (17.6) |
| Minor Amputation | 2 (11.8) |

A comparison of amputation-free survival rates of the present example and treatments known in the art from other studies is given in Table 10.

TABLE 10

| STUDY | BONE MARROW CELLS | BEDSIDE PROCESSING | CELL DOSE | AMPUTATION FREE SURVIVAL | CLAUDICATION PAIN SCORE (VAS) |
|---|---|---|---|---|---|
| CLIRST (Toti, Example 6 herein) | BMC—Bedside Integrated Kit n = 17 | Yes | $1 \times 10^8$ | Major AFS = 82.35% | Before: 7.8; 12 Mo After: 0.5 |
| Harvest Tech. | BMC—Bedside n = 51 | Yes | $3.3 \times 10^9$ | Major AFS = 58% | n/a |
| TACT Study | BMC—Ficoll | No (lab—3 hrs) | $1.6 \times 10^9$ | 3 Yr AFS 60% | Before = 6 Post = 2 p = .0078 |
| Amann Study | BMC—Ficoll n = 12 | No | $1.1 \times 10^9$ | 1 Yr AFS 53% | Not measured. Used analgesic consumption as an endpiint |
| (2 arm study) BONMET-1 | BMC—Bedside n = 39 | Yes | $3.0 \times 10^9$ | 1 Yr AFS 58% | |

As observed in a comparison of the results of previous studies as presented in Table 7, the amputation free survival rate of 82% observed through the practice of the disclosure herein is almost 25% greater than the rate reported through previous studies using techniques that utilize conventional cell populations having bone marrow stem cells.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

What is claimed is:

1. A point-of-care method of ameliorating critical limb ischemia or a condition associated with critical limb ischemia in a subject comprising:
    identifying a subject having a critical limb ischemia or a condition associated with critical limb ischemia;
    providing to said subject a composition comprising:
    (a) a first cell population that comprises $CD34^+$ and $CD34^-$ bone marrow stem cells,
    (b) an anticoagulant, and
    (c) an aqueous buffer and/or an autologous serum and/or an autologous plasma fraction,
    wherein the composition has a viscosity of 1.5 to 5.0 centipoise (cP) measured at 37° C. and wherein said composition is provided to said subject at a rate of 1.0 mL per minute.

2. The method of claim 1, wherein the composition is provided to said subject not more than 2 hours after said first cell population is obtained.

3. The method of claim 1, wherein said composition is provided to said subject not more than 90 minutes after said first cell population is obtained.

4. The method of claim 1, wherein said composition is provided to said subject not more than 60 minutes after said first cell population is obtained.

5. The method of claim 1, wherein the blood flow at an ischemic tissue of said subject is blocked for 1-3 minutes or 2 minutes.

6. The method of claim 5, wherein said blood flow is blocked by an inflatable balloon, wherein said balloon is inflated to block at least 80% of blood flow distal to said balloon.

7. The method of claim 1, wherein said composition provided to said subject is not subjected to a maximum shear of more than 9101/second.

8. The method of claim 1, wherein said composition is provided to said subject through a catheter having a lumen size of approximately 0.36 mm.

9. The method of claim 1, wherein said composition is provided intravascularly or intra-arterially.

10. The method of claim 1, further comprising measuring in said subject an increased blood flow, an increase in angiogenesis, an increase in vascularity, or an increase in amputation-free survival rate.

11. The method of claim 1, wherein said composition is provided to said subject at a pressure of 15-60 psi.

12. The method of claim 1, wherein said composition has a viscosity of 1.8 to 5.0 centipoise (cP) measured at 37° C.

13. The method of claim 1, wherein said $CD34^-$ bone marrow stem cells comprise mesenchymal stem cells or stromal cells.

14. The method of claim 13, wherein said mesenchymal stem cells or stromal cells are lineage negative/dim, CD45 negative/dim and CD73 positive cells.

15. The method of claim 1, wherein said first cell population comprises hematopoietic stem cells, mesenchymal stem cells, stromal cells, endothelial progenitor cells, CXCR4 positive cells, or a combination thereof.

16. The method of claim 1, wherein said composition comprises red blood cells.

17. A point-of-care method of ameliorating critical limb ischemia or a condition associated with critical limb ischemia in a subject comprising:
    identifying a subject having a critical limb ischemia or a condition associated with critical limb ischemia;
    introducing bone marrow aspirate from said subject into a bone marrow processing system;
    isolating a stem cell fraction, a plasma fraction, and a red blood cell fraction from said disposable bone marrow processing device;
    adding plasma from said plasma fraction and red blood cells from said red blood cell fraction to said stem cell fraction to obtain a composition with a viscosity of 1.5 to 5.0 centipoise(cP) measured at 37° C.; and
    providing said composition with a viscosity of 1.5 to 5.0 centipoise (cP) measured at 37° C. to said subject.

18. The method of claim 17, wherein said composition comprises an anticoagulant.

19. The method of claim 17, wherein said stem cell fraction comprises $CD34^+$ and $CD34^-$ bone marrow stem cells.

20. The method of claim 19, wherein said $CD34^-$ bone marrow stem cells comprise mesenchymal stem cells or stromal cells.

21. The method of claim 20, wherein said mesenchymal stem cells or stromal cells are lineage negative/dim, CD45 negative/dim and CD73 positive cells.

22. The method of claim 17, wherein said composition has a viscosity of 1.8 to 5.0 centipoise (cP) measured at 37° C.

23. The method of claim 17, wherein said composition is provided to said subject at a rate of 1.0 to 2.0 mL per minute.

24. The method of claim 17, wherein said composition is provided to said subject at a rate of 1.0 mL per minute.

25. The method of claim 17, wherein said composition is provided to said subject not more than 2 hours after said first cell population is obtained.

26. The method of claim 17, wherein said composition is provided to said subject not more than 90 minutes after said first cell population is obtained.

27. The method of claim 17, wherein said composition is provided to said subject not more than 60 minutes after said first cell population is obtained.

28. The method of claim 17, wherein the blood flow at an ischemic tissue of said subject is blocked by an inflatable balloon, wherein said balloon is inflated to block at least 80% of blood flow distal to said balloon.

29. The method of claim 17, wherein said composition provided to said subject is not subjected to a maximum shear of more than 9101/second.

30. The method of claim 17, wherein said composition is provided to said subject through a catheter having a lumen size of approximately 0.36 mm.

31. The method of claim 17, wherein said composition is provided intravascularly or intra-arterially.

32. The method of claim 17, further comprising measuring in said subject an increased blood flow, an increase in angiogenesis, an increase in vascularity, or an increase in amputation-free survival rate.

33. A point-of-care method of ameliorating critical limb ischemia or a condition associated with critical limb ischemia in a subject comprising:
   identifying a subject having a critical limb ischemia or a condition associated with critical limb ischemia;
   introducing bone marrow aspirate from said subject into a bone marrow processing system that comprises:
   (a) a sterile, disposable bone marrow processing device,
   (b) a control module comprising a gravitational sensor and an infra-red optical sensor coupled with a microprocessor and motor, which are configured to control the flow, movement, and compartmentalization of separated fractions of bone marrow aspirate,
   (c) a docking station that transfers processing data from the control module to a computer, and
   (d) a centrifuge;
   isolating a stem cell fraction, a plasma fraction, and a red blood cell fraction from said disposable bone marrow processing device;
   adding plasma from said plasma fraction and red blood cells from said red blood cell fraction to said stem cell fraction to obtain a composition with a viscosity of 1.5 to 5.0 centipoise (cP) measured at 37° C; and
   providing said composition with a viscosity of 1.5 to 5.0 centipoise (cP) measured at 37° C. to said subject.

34. The method of claim 33, wherein said composition comprises an anticoagulant.

35. The method of claim 33, wherein said stem cell fraction comprises CD34+ bone marrow stem cells and mesenchymal stem cells.

36. The method of claim 33, wherein said stem cell fraction comprises stromal cells.

37. The method of claim 36, wherein said stromal cells are lineage negative/dim, CD45 negative/dim and CD73 positive cells.

38. The method of claim 33, wherein said composition has a viscosity of 1.8 to 5.0 centipoise (cP) measured at 37° C.

39. The method of claim 33, wherein said composition is provided to said subject at a rate of 1.0 to 2.0 mL per minute.

40. The method of claim 33, wherein said composition is provided to said subject at a rate of 1.0 mL per minute.

41. The method of claim 33, wherein said composition is provided to said subject not more than 2 hours after said first cell population is obtained.

42. The method of claim 33, wherein said composition is provided to said subject not more than 90 minutes after said first cell population is obtained.

43. The method of claim 33, wherein said composition is provided to said subject not more than 60 minutes after said first cell population is obtained.

44. The method of claim 33, wherein the blood flow at an ischemic tissue of said subject is blocked by an inflatable balloon, wherein said balloon is inflated to block at least 80% of blood flow distal to said balloon.

45. The method of claim 33, wherein said composition provided to said subject is not subjected to a maximum shear of more than 9101/second.

46. The method of claim 33, wherein said composition is provided to said subject through a catheter having a lumen size of approximately 0.36 mm.

47. The method of claim 33, wherein said composition is provided intravascularly or intra-arterially.

48. The method of claim 33, further comprising measuring in said subject an increased blood flow, an increase in angiogenesis, an increase in vascularity, or an increase in amputation-free survival rate.

49. The method of claim 33, wherein said composition is provided to said subject at a pressure of 15-60 psi.

* * * * *